US008247590B2

(12) United States Patent
Ziche et al.

(10) Patent No.: US 8,247,590 B2
(45) Date of Patent: Aug. 21, 2012

(54) METHOD FOR PREVENTING POLYMERIZATION OF UNSATURATED ORGANOSILICON COMPOUNDS

(75) Inventors: Wolfgang Ziche, Burghausen (DE); Volker Stanjek, Ampfing (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 13/054,179

(22) PCT Filed: Jul. 7, 2009

(86) PCT No.: PCT/EP2009/058617
§ 371 (c)(1),
(2), (4) Date: Jan. 14, 2011

(87) PCT Pub. No.: WO2010/006963
PCT Pub. Date: Jan. 21, 2010

(65) Prior Publication Data
US 2011/0118493 A1    May 19, 2011

(30) Foreign Application Priority Data

Jul. 16, 2008  (DE) .................. 10 2008 040 475

(51) Int. Cl.
*C07F 7/18*    (2006.01)
*C07F 7/20*    (2006.01)
*C07F 7/08*    (2006.01)

(52) U.S. Cl. ........................................ 556/440
(58) Field of Classification Search .......... None
See application file for complete search history.

(56) References Cited

U.S. PATENT DOCUMENTS

| 4,276,429 A | 6/1981 | Lindner |
| 4,563,538 A | 1/1986 | Wakabayashi |
| 4,722,807 A | 2/1988 | Iwahara |
| 4,780,555 A | 10/1988 | Bank |
| 4,894,398 A | 1/1990 | Bank |
| 4,927,948 A | 5/1990 | Bernhardt |
| 5,117,027 A | 5/1992 | Bernhardt et al. |
| 5,145,979 A | 9/1992 | Takatsuna |
| 5,543,538 A | 8/1996 | Haas |
| 5,550,272 A | 8/1996 | Lewis |
| 5,616,753 A | 4/1997 | Turner |
| 5,856,542 A | 1/1999 | Bernhardt |
| 6,441,228 B2 | 8/2002 | Nakahara |
| 2002/0151736 A1 | 10/2002 | Pfeiffer |
| 2010/0179340 A1 | 7/2010 | Lang |

FOREIGN PATENT DOCUMENTS

| DE | 1183503 A | 12/1964 |
| DE | 2238295 A | 2/1973 |
| DE | 3832621 C1 | 9/1989 |
| DE | 4430729 A1 | 3/1996 |
| DE | 10118489 C1 | 7/2002 |
| DE | 102007023760 A1 | 5/2007 |
| EP | 0483480 A1 | 5/1992 |
| EP | 0520477 A1 | 12/1992 |
| EP | 0708081 B1 | 4/1996 |
| EP | 0845465 A2 | 6/1998 |
| EP | 0845471 A2 | 6/1998 |
| GB | 1003874 A | 9/1965 |
| GB | 1364360 A | 8/1974 |
| WO | 2005040084 A1 | 5/2005 |

*Primary Examiner* — Yevegeny Valenrod
(74) *Attorney, Agent, or Firm* — Brooks Kushman P.C.

(57) ABSTRACT

Undesired polymerization of (meth)acrylatoalkoxysilanes during their industrial preparation and handling is accomplished by avoiding contact with surfaces containing more than 1% by weight of iron.

9 Claims, No Drawings

METHOD FOR PREVENTING POLYMERIZATION OF UNSATURATED ORGANOSILICON COMPOUNDS

CROSS-REFERENCE TO RELATED APPLICATION

This application is the U.S. national phase of PCT Appln. No. PCT/EP2009/058617 filed Jul. 7, 2009 which claims priority to German application DE 10 2008 040 475.6 filed Jul. 16, 2008.

BACKGROUND OF THE INVENTION

1. Field of the Invention

The present invention relates to an industrial method for preventing the polymerization of unsaturated organosilicon compounds in the preparation and handling thereof 2. Description of the Related Art Organosilicon compounds having unsaturated organic functional groups, e.g. vinyl, acryl or methacryl groups, are widely employed as bonding agents between inorganic and organic materials, e.g. in sizes for glass fibers, as crosslinkers in organic polymers or for the treatment of fillers.

Processes for preparing such compounds comprise, for example, the reaction catalyzed by metal compounds between silanes having SiH bonds and multiply unsaturated organic compounds. A further customary route is reaction of chloroalkylsilanes with alkali metal (meth)acrylates. All these processes proceed exothermically at elevated temperatures. There is therefore a risk of polymerization of the products via the unsaturated organic group during the reaction, as a result of which product is lost and reaction apparatuses used have to be subjected to costly cleaning.

In addition, the silanes bearing unsaturated organic groups are usually purified by distillation, which likewise entails a considerable polymerization risk due to the thermal stress necessary for the distillation. Finally, there is also a risk of polymerization during storage of these compounds.

Various methods of minimizing the risk of polymerization of organosilicon compounds having unsaturated organic groups are known. U.S. Pat. No. 4,276,426 describes, for example, the synthesis of 3-methacryloxypropylsilanes from allyl methacrylate and various silanes having SiH bonds with rapid pump circulation of the reactants in a loop reactor, as a result of which polymerization can be prevented.

Numerous methods of preventing the polymerization of organosilicon compounds bearing unsaturated organic groups involve the use of free-radical polymerization inhibitors: DE 11 83 503 describes stabilization by addition of 50-500 ppm of hydroxyphenyl compounds such as hydroquinone or hydroquinone monomethyl ether together with 0.5-10% by weight of an alcohol which is soluble in water and the silane. DE 22 38 295 describes the use of quinones together with the corresponding enols. U.S. Pat. No. 4,563,538 describes stabilization of the unsaturated organosilicon compounds by means of 2,6-di-tert-butylbenzoquinone, while a combination of 2,6-di-tert-butylhydroquinone and methanol is used in U.S. Pat. No. 4,722,807. Another way is described in U.S. Pat. No. 4,894,398: here, stabilization of the unsaturated organosilicon compound is effected by addition of a sufficient amount of a hydroxylamine. DE 38 32 621 C1 describes the combination of two different polymerization inhibitors, consisting of a compound from the class of N,N'-disubstituted p-phenylenediamines and a compound from the class of 2,6-di-tert-butyl-4-alkylphenols. U.S. Pat. No. 4,780,555 describes a further method of preventing the polymerization of unsaturated organosilicon compounds: here, the combination of phenothiazine together with a gas atmosphere containing at least 0.1% by volume of oxygen, which is brought into contact with the unsaturated organosilicon compound, effects stabilization. A disadvantage of this method is the need for a defined amount of oxygen to be present, which is technically complicated, especially during a distillation, and is also disadvantageous in terms of safety. A further combination of compounds, which is described as having a stabilizing effect in U.S. Pat. No. 5,145,979, is a mixture of a sterically hindered phenol, an aromatic amine and an alkylamine. Further compounds which can be used for stabilizing organosilicon compounds bearing unsaturated organic functional groups are, for example, specific 2,6-dialkyl-4-N,N-dialkylaminomethylphenols, either alone or in combination with other compounds having a stabilizing effect (EP 0 520 477 B1), tertiary amines (DE 44 30 729 A1), nonaromatic, stable free radicals such as 2,2,6,6-tetramethylpiperidinyl oxide ("TEMPO", U.S. Pat. No. 5,616,753, U.S. Pat. No. 5,550,272), N,N'-disubstituted p-quinodiimines (EP 0 708 081 B1), dialkylamides of unsaturated organic acids (e.g. in EP 0 845 471 A2), zinc salts of 2-mercaptobenzothiazole or dimethyldithiocarbamate (e.g. in EP 0 845 465 A2).

All the methods described have the disadvantages that relatively large amounts of stabilizing compound have to be added, generally 50-2000 ppm by weight based on the weight of the silane, that these compounds are often quite expensive, and that the methods described are often, as in the case of contacting with an oxygen-containing gas mixture, problematic in terms of safety. Furthermore, most of the compounds described still involve the risk, despite a stabilizing effect on unsaturated organosilicon compounds, that the unsaturated organosilicon compound will polymerize and thereby be lost. Finally, a further disadvantage is the fact that most of the compounds described as polymerization inhibitors are solids which can only be metered using complicated working steps or apparatuses.

U.S. Pat. No. 6,441,228 B2 describes the use of molybdenum-containing steel alloys in the synthesis of methacrylic acid. WO 2005/40084 describes the use of copper-containing alloys for the preparation, purification, handling or storage of ethylenically unsaturated compounds. A disadvantage here is the use of unconventional alloys.

SUMMARY OF THE INVENTION

It was therefore an object of the present invention to develop a method of preparing, purifying, handling or storing unsaturated organosilicon compounds, which is suitable for industrial production and does not have the disadvantages of the prior art. These and other objects are surprisingly achieved by processing in an industrial apparatus, at least 70% of the surfaces of which come in contact with the unsaturated organosilicon compound contain less than 1% iron.

DETAILED DESCRIPTION OF THE PREFERRED EMBODIMENTS

The invention thus provides a method of preventing polymerization in the preparation or handling of unsaturated organosilicon compounds (S) of the general formula (1)

$$H_2C=C(R^1)[C(O)O]_w(O)_x-(R^2)_y-Si(R^3)_z(OR^4)_{3-z} \qquad (1)$$

where
R$^1$ is a hydrogen atom or a linear or branched hydrocarbon radical having 1-10 carbon atoms,

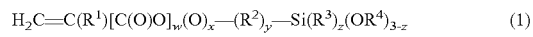

$R^2$ is a linear or branched hydrocarbon radical which has 1-40 carbon atoms and may contain one or more heteroatoms selected from among the elements nitrogen, oxygen, sulfur and phosphorus, $R^3$ and $R^4$ are linear or branched hydrocarbon radicals having 1-10 carbon atoms, w can be 0 or 1, x can be 0 or 1, y can be 0 or 1 and z can be 0, 1 or 2, where w and x must not at the same time be 1, wherein at least one step of the preparation or handling is carried out in an industrial apparatus (A) whose surfaces which come into contact with the organosilicon compounds (S) comprise at least 70% of an iron-free material, where a material is designated as iron-free when it contains less than 1% by weight of iron, and the industrial apparatus (A) is either an apparatus for a batch process having a fill volume of at least 200 l or an apparatus for a continuous process having a throughput of at least 15 l/h.

When iron-free materials are used, the polymerization of organosilicon compounds (S) is greatly slowed or completely prevented during the preparation or handling thereof.

The method prevents polymerization in all preparative or handling steps such as synthesis; purification such as separation of a solid from the organosilicon compound (S) by filtration, distillative purification of the organosilicon compound (S) by removal of low-boiling impurities or distillative purification of the organosilicon compound (S) by distillation of the organosilicon compound (S) itself; transport and storage; and further processing to produce downstream products.

The surfaces of the apparatus (A) which come into contact with the organosilicon compound (S) preferably comprise at least 90% and more preferably 99% of an iron-free material. Here, the term iron-free means that the respective material contains less than 1% by weight of iron, preferably less than 0.1% by weight, more preferably less than 0.01% by weight, and in particular less than 0.001% by weight, of iron.

Examples of iron-free materials are glass, enamels, nickel, copper, titanium, zirconium, niobium, tantalum and alloys thereof having an iron content of <0.5% by weight, plastics such as PTFE, graphite, oxide ceramics such as aluminum oxide, silicon carbide and silicon nitride. Preference is given to metal-free materials such as glass, enamels, plastics such as PTFE, graphite, oxide ceramics such as aluminum oxide, silicon carbide and silicon nitride. Particular preference is given to glass, enamels, graphite, oxide ceramics such as aluminum oxide, silicon carbide and silicon nitride, in particular glass, enamels and graphite.

The synthesis of the unsaturated organosilicon compounds (S) can be carried out in various ways. Thus, the reaction of unsaturated organic compounds such as ethyne or allyl methacrylate with silicon compounds having Si—H bonds in the presence of catalysts, e.g. platinum compounds, leads to the desired unsaturated organosilicon compounds (S).

Particular preference is given to the synthesis in which silanes (S) of the general formula (2)

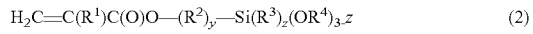  (2)

are prepared from a haloalkylsilane of the general formula (3)

  (3)

and a salt of a (meth)acrylate having anions of the general formula (4)

  (4)

where X is a halogen atom and all other variables are as defined for the general formula (1).

This synthesis is frequently carried out in the presence of a phase transfer catalyst. Examples of such phase transfer catalysts are tetraorganoammonium or tetraorganophosphonium salts. The reaction is preferably carried out at temperatures in the range from 60 to 150° C. and more preferably at temperatures in the range from 70 to 120° C. The halogen salts formed as by-product and any residues of the (meth)acrylate salts with anions of the general formula (4) which may be present are preferably separated off by filtration. The product is then preferably purified by distillation, with one or more purification steps being carried out.

Low-boiling impurities are preferably separated off first by distillation. This preferably occurs under reduced pressure and at temperatures in the range from 20 to 120° C., preferably from 40 to 80° C. The silane (S) of the general formula (2) itself may subsequently be distilled, with this distillation step, too, preferably being carried out under reduced pressure so that the temperature at the bottom during the distillation is below 200° C., preferably below 150° C. and most preferably below 130° C.

In the general formulae (1) to (4), $R^1$ is preferably a hydrogen atom or an alkyl radical having 1-3 carbon atoms, in particular $CH_3$; $R^2$ is preferably an alkyl radical having 1-6 carbon atoms, in particular a $CH_2$ or $(CH_2)_3$ group; $R^3$ is preferably $CH_3$ or an ethyl radical; and $R^4$ is preferably a methyl, ethyl, propyl or isopropyl radical, with particular preference being given to methyl and ethyl radicals. X is preferably chlorine or bromine, particularly more preferably chlorine.

In the preparation or handling of the unsaturated organosilicon compounds (S), conventional stabilizers such as hydroquinone, hydroquinone monomethyl ether, phenothiazine, N,N-disubstituted aminomethylenephenols and/or oxygen can be present.

Examples of apparatuses (A) for the preparation or handling of unsaturated organosilicon compounds (S) of the general formula (1) or (2) are stirred vessels, tube reactors, distillation columns and internals and packings therein, thin film evaporators, falling film evaporators, short path distillations, including internals thereof, e.g. wipers in thin film evaporators, and also heat exchangers and tanks.

In a preferred embodiment of the invention, the apparatuses (A) are stirred vessels for a batch synthesis and/or distillation of the organosilicon compounds (S) having a fill volume of at least 200 l, with particular preference being given to fill volumes of at least 500 l or at least 1000 l.

In a further preferred embodiment of the invention, the apparatuses (A) are reactors for a continuous synthesis having a throughput of at least 15 l/h, with particular preference being given to throughputs of at least 30 l/h or at least 100 l/h.

In a further preferred embodiment of the invention, the apparatuses (A) are thin film evaporators, falling film evaporators or short path distillations having a throughput of at least 15 l/h, with particular preference being given to throughputs of at least 30 l/h or at least 50 l/h.

The process steps carried out in apparatuses (A) are preferably those in which the unsaturated organosilicon compounds (S) of the general formula (1) or (2) are thermally stressed, e.g. the synthesis and the purification by distillation. The purification by distillation is particularly preferably carried out in apparatuses (A). Preference is given here to using an apparatus (A) for a batch distillation, more preferably a thin film, falling film or short path evaporator. The thin film, falling film or short path evaporator may in this case be of a single-stage design, e.g. when only the low boilers have to be removed to achieve sufficient purification of the product, or else in a two-stage process the low boilers are separated off first and the product itself is distilled in the second pass through an evaporator. It is likewise possible to use a two-stage thin film, falling film or short path evaporator, with the low boilers being removed in the first stage and the product itself being distilled in the second stage. In this case, any thin film evaporator stage represents an apparatus (A) for the purposes of the present invention. In a preferred embodiment, only one of the two thin film evaporator stages consists of an apparatus (A), but preference is given to both thin film evaporator stages being apparatuses (A).

In a preferred process, at least two of the process steps selected from the synthesis of organosilicon compounds (S), separation of a solid from the organosilicon compounds (S) by filtration, distillative purification of the organosilicon compounds (S) by removal of low-boiling impurities or distillative purification of the organosilicon compounds (S) by distillation of the organosilicon compounds (S) themselves are carried out in an industrial apparatus (A) having the abovementioned properties. Particular preference is given to carrying out all process steps in such apparatuses (A).

Examples of unsaturated organosilicon compounds (S) of the general formula (1) are vinylsilanes such as vinyltrimethoxysilane, vinyltriethoxysilane, vinyltriphenyloxysilane, vinyltriisopropoxysilane, vinyltris(2-methoxyethoxy)silane, vinyl(dimethoxy)methylsilane, vinyl(diethoxy)methylsilane, vinyl(diphenyloxy)methylsilane, vinyl(diisopropoxy)methylsilane, vinylbis(2-methoxyethoxy)methylsilane, allylsilanes such as allyltrimethoxysilane, allyltriethoxysilane, allyltriphenyloxysilane, allyltriisopropoxysilane, allyltris(2-methoxyethoxy)silane, allyl(dimethoxy)methylsilane, allyl(diethoxy)methylsilane, allyl(diphenyloxy)methylsilane, allyl(diisopropoxy)methylsilane, allylbis(2-methoxyethoxy)methylsilane, 3-allyloxypropyltrimethoxysilane, 3-allyloxypropyltriethoxysilane, 3-allyloxypropyltriphenyloxysilane, 3-allyloxypropyltriisopropoxysilane, 3-allyloxypropyltris(2-methoxyethoxy)silane, acrylsilanes such as acryloxymethyltrimethoxysilane, acryloxymethyltriethoxysilane, acryloxymethyltriphenyloxysilane, acryloxymethyltriisopropoxysilane, acryloxymethyltris(2-methoxyethoxy)silane, acryloxymethyl(methyl)dimethoxysilane, acryloxymethyl(methyl)diethoxysilane, acryloxymethyl(methyl)diphenyloxysilane, acryloxymethyl(methyl)diisopropoxysilane, acryloxymethyl(methyl)bis(2-methoxyethoxy)silane, acryloxymethyl(dimethyl)methoxysilane, acryloxymethyl(dimethyl)ethoxysilane, acryloxymethyl(dimethyl)phenyloxysilane, acryloxymethyl(dimethyl)isopropoxysilane, acryloxymethyl(dimethyl)(2-methoxyethoxy)silane, 3-acryloxypropyltrimethoxysilane, 3-acryloxypropyltriethoxysilane, 3-acryloxypropyltriphenyloxysilane, 3-acryloxypropyltriisopropoxysilane, 3-acryloxypropyltris(2-methoxyethoxy)silane, 3-acryloxypropyl(methyl)dimethoxysilane, 3-acryloxypropyl(methyl)diethoxysilane, 3-acryloxypropyl(methyl)diphenyloxysilane, 3-acryloxypropyl(methyl)diisopropoxysilane, 3-acryloxypropyl(methyl)bis(2-methoxyethoxy)silane, 3-acryloxypropyl(dimethyl)methoxysilane, 3-acryloxypropyl(dimethyl)ethoxysilane, 3-acryloxypropyl(dimethyl)phenyloxysilane, 3-acryloxypropyl(dimethyl)isopropoxysilane, 3-acryloxypropyl(dimethyl)(2-methoxyethoxy)silane or methacrylsilanes such as methacryloxymethyltrimethoxysilane, methacryloxymethyltriethoxysilane, methacryloxymethyltriphenyloxysilane, methacryloxymethyltriisopropoxysilane, methacryloxymethyltris(2-methoxyethoxy)silane, methacryloxymethyl(methyl)dimethoxysilane, methacryloxymethyl(methyl)diethoxysilane, methacryloxymethyl(methyl)diphenyloxysilane, methacryloxymethyl(methyl)diisopropoxysilane, methacryloxymethyl(methyl)bis(2-methoxyethoxy)silane, methacryloxymethyl(dimethyl)methoxysilane, methacryloxymethyl(dimethyl)ethoxysilane, methacryloxymethyl(dimethyl)phenyloxysilane, methacryloxymethyl(dimethyl)isopropoxysilane, methacryloxymethyl(dimethyl)(2-methoxyethoxy)silane, 3-methacryloxypropyltrimethoxysilane, 3-methacryloxypropyltriethoxysilane, 3-methacryloxypropyltriphenyloxysilane, 3-methacryloxypropyltriisopropoxysilane, 3-methacryloxypropyltris(2-methoxyethoxy)silane, 3-methacryloxypropyl(methyl)dimethoxysilane, 3-methacryloxypropyl(methyl)diethoxysilane, 3-methacryloxypropyl(methyl)diphenyloxysilane, 3-methacryloxypropyl(methyl)diisopropoxysilane, 3-methacryloxypropyl(methyl)bis(2-methoxyethoxy)silane, 3-methacryloxypropyl(dimethyl)methoxysilane, 3-methacryloxypropyl(dimethyl)ethoxysilane, 3-methacryloxypropyl(dimethyl)phenyloxysilane, 3-methacryloxypropyl(dimethyl)isopropoxysilane, 3-methacryloxypropyl(dimethyl)(2-methoxyethoxy)silane.

Examples of particularly preferred unsaturated organosilicon compounds (S) of the general formula (2) are those in which $R^2$ is a methylene group. These silanes often have a particularly high reactivity and, associated therewith, a particularly high tendency to polymerize. Very particular preference is given to: acryloxymethyltrimethoxysilane, acryloxymethyltriethoxysilane, acryloxymethyl(methyl)dimethoxysilane, acryloxymethyl(methyl)diethoxysilane, acryloxymethyl(dimethyl)methoxysilane, acryloxymethyl(dimethyl)ethoxysilane, methacryloxymethyltrimethoxysilane, methacryloxymethyltriethoxysilane, methacryloxymethyl(methyl)dimethoxysilane, methacryloxy(methyl)diethoxysilane, methacryloxymethyl(dimethyl)methoxysilane and methacryloxymethyl(dimethyl)ethoxysilane.

All the above symbols in the above formulae have their meanings independently of one another. In all formulae, the silicon atom is tetravalent.

In the following examples and comparative examples, all amounts and percentages are, unless indicated otherwise, by weight and all reactions are carried out at a pressure of 0.10 MPa (abs.) and a temperature of 20° C. BHT is butylhydroxytoluene (3,5-di-tert-butyl-4-hydroxytoluene).

Comparative Example 1

A crude batch of methacryloxymethyldimethoxymethylsilane (contains 3500 ppm of KOH) stabilized with 200 ppm of BHT and 200 ppm of phenothiazine was heated in air at 150° C. in a glass flask in the presence of stainless steel wool. The product gelled after 60 minutes.

Example 2

A crude batch of methacryloxymethyldimethoxymethylsilane (contains 3500 ppm of KOH) stabilized with 200 ppm of BHT and 200 ppm of phenothiazine was heated in air at 150° C. in a glass flask in the absence of stainless steel wool. The product gelled after 180 minutes.

Comparative Example 3

A crude batch of methacryloxymethyldimethoxymethylsilane (neutralized with methanesulfonic acid) stabilized with 200 ppm of BHT and 200 ppm of phenothiazine was heated in air at 150° C. in a glass flask in the presence of stainless steel wool. The product gelled after 2 hours 20 minutes.

Comparative Example 4

A crude batch of methacryloxymethyldimethoxymethylsilane (neutralized with phosphoric acid) stabilized with 200 ppm of BHT and 200 ppm of phenothiazine was heated in air at 150° C. in a glass flask in the presence of stainless steel wool. The product gelled after 6 hours.

Example 5

A crude batch of methacryloxymethyldimethoxymethylsilane (neutralized with methanesulfonic acid) stabilized with 200 ppm of BHT and 200 ppm of phenothiazine was heated in air at 150° C. in a glass flask in the absence of stainless steel wool. The product gelled after 7 hours.

Comparative Example 6

A crude batch of methacryloxymethyldimethoxymethylsilane (neutralized with phosphoric acid) stabilized with 200 ppm of BHT, 200 ppm of phenothiazine and 200 ppm of copper acetylacetonate was heated in air in a glass flask in the presence of stainless steel wool. The product gelled on heating to 120° C.

These laboratory-scale experiments show the influence of an iron-containing material on the stability.

Example 7

Production in Enamel Vessel

A crude batch of methacryloxymethyldimethoxymethylsilane is prepared as described in DE 101,18,489 C1, but in an enameled stirred vessel from 200 kg of chloromethyl-dimethoxymethylsilane and potassium methacrylate.

Polymer formation is checked as follows:

1.5 ml of methacrylsilane are placed in a 20 ml snap-top bottle, 6 ml of isohexane are then added thereto and 6 ml of water are introduced as a layer under the mixture. The bottle is closed and shaken. After phase separation, the two-phase solution remains clear. 3 l of the crude batch are purified in a glass short path distillation (type) (80° C., 0.2 mbar). The bottoms are homogenous and have a low viscosity.

Comparative Example 8

Production in Steel Vessel

A crude batch of methacryloxymethyldimethoxymethylsilane is prepared as described in DE 101,18,489 C1 in an unenameled stirred vessel made of VA steel from 200 kg of chloromethyldimethoxymethylsilane and potassium methacrylate.

1.5 ml of methacrylsilane are placed in a 20 ml snap-top bottle, 6 ml of isohexane are then added thereto and 6 ml of water are introduced as a layer under the mixture. The bottle is closed and shaken. After phase separation, a lump of polymer is formed at the interface of the two phases.

3 l of the crude batch are purified in a glass short path distillation (type) (80° C., 0.2 mbar). The bottoms have gel-like lumps and are distinctly viscous.

Comparative Example 9

Distillation Using Steel Short Path Distillation

The crude batch from example 7 is distilled via a two-stage short path distillation (VA steel with graphite/PTFE wiper blades, evaporator area 0.25 m², temperature 80° C., vacuum 0.2 mbar, throughput 25 kg/h). After 60 minutes, increased formation of polymer occurs, so that production is stopped.

Example 10

Distillation Using Glass Short Path Distillation

The crude batch from example 7 is distilled via a single-stage short path distillation made of glass (QVF (Mainz, Deutschland), evaporator area 0.6 m², temperature 120° C., vacuum 13 mbar, throughput 24 kg/h). The product can be distilled without formation of polymers.

The invention claimed is:

1. A method of preventing polymerization in the preparation or handling of unsaturated organosilicon compounds (S) of the formula (2)

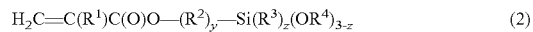

which are prepared from a haloalkylsilane of the formula (3)

and a salt of a (meth)acrylate having anions of the formula (4)

in the presence of stabilizers,
where X is a halogen atom,
$R^1$ is a hydrogen atom or a linear or branched hydrocarbon radical having 1-10 carbon atoms,
$R^2$ is a linear or branched hydrocarbon radical which has 1-40 carbon atoms optionally containing one or more nitrogen, oxygen, sulfur or phosphorus heteroatoms,
$R^3$ and $R^4$ are linear or branched hydrocarbon radicals having 1-10 carbon atoms,
y is 0 or 1 and
z is 0, 1 or 2,
wherein at least the synthesis of the organosilicon compounds (S) and the distillative purification of the organosilicon compounds (S) is carried out in an industrial apparatus (A), at least 70% of whose surfaces which come into contact with the organosilicon compounds (S) comprise an iron-free material, where a material is designated as iron-free when it contains less than 1% by weight of iron, and is selected from the group consisting of glass, enamel, plastic, graphite, oxide ceramics, silicon carbide, silicon nitride, and mixtures thereof,
and the industrial apparatus (A) is either an apparatus for a batch process having a fill volume of at least 200 l or an apparatus for a continuous process having a throughput of at least 15 l/h.

2. The method of claim 1, wherein at least 99% of the surfaces of the apparatus (A) which come into contact with the organosilicon compound (S) comprise a material containing less than 0.1% by weight of iron.

3. The method of claim 1, wherein $R^1$ is a hydrogen atom or $CH_3$.

4. The method of claim 1, wherein $R^2$ is a $CH_2$ or $(CH_2)_3$ group.

5. The method of claim 1, wherein $R^3$ is a methyl or ethyl radical.

6. The method of claim 1, wherein $R^4$ is a methyl or ethyl radical.

7. The method of claim 1, wherein the industrial apparatus (A) comprises a thin film evaporator, falling film evaporator or short path distillation having a throughput of at least 15 l/h.

8. The method of claim 1, wherein the industrial apparatus (A) is an apparatus for a batch process having a fill volume of at least 1000 l or an apparatus for a continuous process having a throughput of at least 100 l/h.

9. The method of claim 1, further comprising carrying out all processing steps in apparatuses having at least 70% of their surfaces containing less than 1% iron.

* * * * *